United States Patent [19]

Jarvis, Jr.

[11] Patent Number: 4,582,799

[45] Date of Patent: Apr. 15, 1986

[54] PROCESS FOR RECOVERING NONSECRETED SUBSTANCES PRODUCED BY CELLS

[75] Inventor: Allan P. Jarvis, Jr., Newburyport, Mass.

[73] Assignee: Damon Biotech, Inc., Needham Heights, Mass.

[21] Appl. No.: 485,472

[22] Filed: Apr. 15, 1983

[51] Int. Cl.[4] .................. C12P 21/00; C12N 11/10; C12N 5/02; A01N 63/00

[52] U.S. Cl. .................................. 435/68; 435/178; 435/182; 435/241; 435/803; 424/93; 424/DIG. 7

[58] Field of Search ............... 435/4, 68, 29, 30, 241, 435/242, 178, 182, 803; 424/DIG. 7, 93

[56] References Cited

U.S. PATENT DOCUMENTS

| | | | |
|---|---|---|---|
| 3,522,346 | 7/1970 | Chang | 424/35 |
| 3,725,113 | 4/1973 | Chang | 424/35 |
| 3,730,841 | 5/1973 | Forgione et al. | 435/182 |
| 3,733,205 | 5/1973 | Shovers | 426/62 |
| 3,827,565 | 8/1974 | Matsumora | 210/632 |
| 3,860,490 | 1/1975 | Guttag | 435/182 |
| 4,138,292 | 2/1979 | Chibata | 435/178 |
| 4,251,387 | 2/1981 | Lim et al. | 252/316 |
| 4,391,909 | 7/1983 | Lim | 435/178 |
| 4,409,331 | 10/1983 | Lim | 435/178 |

FOREIGN PATENT DOCUMENTS 1600988  9/1970  France .

OTHER PUBLICATIONS

Alberts, B., D. Bray, J. Lewis, M. Raff, K. Roberts and J. Watson, 1983 Molecular Biology of the Cell, pp. 265-266, Garland Publishing Inc.

Biotechnology & Bioengineering, vol. XIX, p. 387; M. Kierstan & C. Bucke (1977).

*Primary Examiner*—Robert J. Warden
*Assistant Examiner*—Cynthia Lee Foulke
*Attorney, Agent, or Firm*—Lahive & Cockfield

[57] ABSTRACT

Disclosed is a process for recovering nonsecreted substances produced by cells. The process eliminates some of the high molecular weight contaminants thereby simplifying the purification process. The cells are encapsulated within a semipermeable membrane having properties which permit rapid passage of the relatively low molecular weight substances of interest but retard or prevent passage of higher molecular weight contaminants. The encapsulated cells are suspended in a culture medium and undergo normal cell growth and mitosis. The encapsulated cell culture grows to substantially fill the capsules but not rupture them. The cell membrane is then lysed without disrupting the capsule membrane. The permeability of the capsule membrane is such that the substances of interest diffuse rapidly through the capsule membrane into the extracapsular fluid while the higher molecular weight contaminants and cell fragments are retained within the capsule. The process is particularly useful for obtaining low to moderate molecular weight substances produced by pyrogen-producing prokaryotic, genetically modified organisms because the crude product can be collected relatively free of high molecular weight pyrogenic contaminants.

29 Claims, 5 Drawing Figures

PROCESS FOR RECOVERING NONSECRETED SUBSTANCES PRODUCED BY CELLS

BACKGROUND OF THE INVENTION

This invention relates to a method of purifying biological material produced by cells. More particularly, the invention relates to a process for recovering nonsecreted substances produced by cells free of many unwanted high molecular weight contaminants.

Advances in cellular biology have demonstrated that the concentration of a number of active biological substances is substantially greater inside the cell than in the surrounding media. These substances, whether because of their molecular weight, charge, or other reasons, are not easily transported across the cell membrane or are simply not secreted by the cell. Any process for recovering these products requires disrupting or lysing the cell membrane. Upon cell lysis, the media is contaminated with cell fragments and unwanted high molecular weight contaminants. Since the concentration of the non-secreted substance is relatively small compared with the total concentration of cell components, recovery of the substance of interest may be difficult. The phrase nonsecreted substance, as used herein, means a substance which is produced in significant recoverable quantities within the cell which is not secreted or only partially secreted.

An associated problem is the release from cells of pyrogens; fever-inducing substances, during cell lysis. Many prokaryotic bacteria, particularly the gram negative enterobacteria, produce endotoxins which are pyrogenic. Since these gram negative bacteria, e.g., E. coli, bacillus, and pseudomonas are the basic bacteria used in DNA recombinant technology, the pyrogenic endotoxins produced by these bacteria are a serious problem. These pyrogenic substances are primarily lipopolysaccharides having molecular weights greater than $5 \times 10^4$ daltons. A number of enzymes and other nonsecreted substances of interest have lower molecular weights than the pyrogens, so a method for molecular sieving of contaminants released upon cell lysis would assist in purification and recovery.

U.S. Pat. No. 4,352,883 discloses a method for producing microcapsules containing viable cells. Copending U.S. application Ser. No. 372,835 now U.S. Pat. No. 4,409,331 takes this encapsulation procedure a step further and discloses a process for producing substances produced by cells. More particularly, the U.S. Pat. No. 4,409,331 discloses that low molecular weight substances secreted by cells can diffuse through the semipermeable membrane of the microcapsule and can be collected in the extracapsular media with a minimum of contamination and that higher molecular weight substances secreted by cells can be trapped within the microcapsules and can be collected by disrupting the capsule membrane without lysing the cells.

Accordingly, an object of the invention is to provide a method for recovering nonsecreted substances substantially free of contaminants. Another object of the invention is to provide a method for substantially pyrogen-free recovery of nonsecreted substances from pyrogen-producing microorganisms. A further object is to provide a method of lysing the cell membranes of encapsulated cells without disrupting the membrane of the surrounding microcapsule. A still further object of the invention is to provide a method for recovery of low molecular weight, nonsecreted substances from genetically modified bacteria.

These and other objects and features of the invention will be apparent from the following description and from the drawings.

SUMMARY OF THE INVENTION

This invention provides a method of recovery of non-secreted substances produced by cells as a crude product having a reduced concentration of high molecular weight contaminants and higher specific activity. The invention is particularly useful for recovery of low molecular weight, nonsecreted substances produced by natural or genetically modified pyrogen-producing bacteria. The process of the invention comprises the steps of encapsulating a cell within a membrane having permeability properties which permit rapid passage of the lower molecular weight substance of interest while retarding or preventing passage of unwanted higher molecular weight contaminants. The encapsulated cell is suspended in an aqueous culture medium and is allowed to undergo metabolism, cell growth, and mitosis within the capsule membrane. The medium used is preferably a growth medium sufficient to support mitosis of the encapsulated cells, but may also be an aqueous culture medium sufficient to support biosynthesis of said substance. A cell colony is formed which multiplies to substantially fill the capsule volume but does not rupture the microcapsule membrane. The cell membrane is then lysed without disrupting the capsule membrane and the substance of interest diffuses through the capsule membrane into the surrounding extracapsular fluid where it is harvested as a crude product. The preferred means for lysing the cell membrane is by suspending the capsules in a detergent which does not disrupt the capsule membrane.

Prokaryotic cells, either natural or genetically modified, are the preferred cells for use in the process because the process is particularly useful for recovering substances produced by pyrogen-producing cells. The majority of the high molecular weight pyrogens, such as endotoxins, remain within the capsule while the lower molecular weight substances diffuse rapdily through the pores of the capsule membrane. The membrane pores comprise tortuous paths which allow the low molecular weight substances of interest to pass through the membrane while retaining the unwanted high molecular weight contaminants.

DESCRIPTION

In its broadest aspect, the invention features a process for recovering nonsecreted substances produced by cells in a partially purified state by retaining high molecular weight contaminants including cell fragments, nucleic acids, polysaccharides, lipids and proteins inside a semipermeable membrane while allowing the nonsecreted, relatively low molecular weight substances to diffuse across the membrane.

The process is applicable to any cell system which produces a substance of interest having a molecular weight lower than the molecular weight of the potential contaminants. The process is particularly well adapted for culturing prokaryotic cells, either naturally occurring or genetically modified, as the source of the nonsecreted substance. The nutrient requirements for prokaryotic cells are primarily low molecular weight molecules which are easily transported across the semipermeable membrane facilitating cell growth and mitosis which leads to a larger production of the substance of interest. The cell colonies reproduce until they substantially fill the capsules yet do not rupture the capsule membrane.

As previously noted, most of the recombinant DNA techniques have used gram negative enterobacteria as the host organism. Many of these bacteria produce pyrogenic endotoxins which are released on cell lysis. In order to obtain a substance of interest produced by these pyrogenic cultures in a useable form, the pyrogens normally must be eliminated. Substantially all of the pyrogins have a molecular weight greater than $5 \times 10^4$ daltons. Accordingly, a semipermeable membrane having permeability properties which allows the transport of molecules at a rate which is an inverse function of their molecular weight, or precludes transport of high molecular weight contaminants, can significantly promote purification of lower molecular weight products.

Another positive aspect of the present invention is the ease of maintaining culture sterility and thereby diminishing the possibility of contamination of the culture or the product. Since the amount of substance produced by the cells is very small, any contamination of the culture is a major problem. Encapsulation provides a physical barrier against contamination.

The process is applicable to a wide variety of substances produced by cells, particularly relatively small molecular weight materials. Exemplary pyrogens which may be eliminated by this procedure include such endotoxins as the lipoproteins produced by *E. coli*. One limitation on effectiveness of the process is that the substance of interest must have a molecular weight smaller than the pyrogen or other contaminants sought to be excluded.

The process of the invention depends, in part, on one's ability to encapsulate cells in a semipermeable membrane without adversely affecting their ongoing viability. One suitable encapsulation technique is set forth below in detail.

CELL ENCAPSULATION

The following microencapsulation technique, a variation of the preferred technique disclosed in U.S. Pat. No. 4,352,883, has been used successfully to produce viable cell cultures. Ongoing viability of the cell culture requires that sufficient nutrients and oxygen are transported across the encapsulating membrane. The microcapsule membrane also excludes contaminating bacteria from the culture. The capsule membranes must be formed in pH conditions which do not affect cell viability. The microcapsules can vary widely in size but best results have been obtained with capsules ranging from 100–1000 micrometers.

To encapsulate the cells, a water-soluble substance, physiologically compatible with the cells, which can be rendered water-insoluble forms a shape-retaining, coherent mass or "temporary matrix" about individual cells or a group of cells. This "temporary matrix" can then be treated to deposit a more permanent semipermeable membrane about the cell while insuring cell viability. The water-soluble substance is added, typically on the order of 0.5–2 percent, to a suspension of the cells in saline and the resulting mixture is formed into droplets. The droplets are rendered water-insoluble and gelled to form the temporary matrix. This temporary matrix is provided with a more permanent capsule membrane and, preferably, the capsule interior is reliquified by establishing the conditions under which the water-soluble substance was liquid. The reliquification step allows mass transport of nutrients and cell growth.

The material used to form the temporary matrix may be any non-toxic, water-soluble material which, by change in ionic environment or concentration, can be converted to a shape-retaining mass. The material should also contain plural, easily ionized anionic moieties, e.g., carboxyl groups, which can react by salt formation with polymers containing plural cationic groups. As will be explained below, use of this type of material enables one to deposit a permanent capsule membrane of a selected upper limit of permeability without difficulty in surface layers of the temporary matrix.

The presently preferred materials for forming the temporary mixture are acidic, water-soluble, natural or synthetic polysaccharide polymers or gums. Such materials are commercially available. They are typically extracted from vegetable matter and are often used as additives to various foods. Sodium alginate is the presently preferred water-soluble gum. Alginate in the molecular weight range of 150,000+ daltons may be used, but because of its molecular dimensions and viscosity will usually be unable to permeate the finally formed capsule membranes. Lower molecular weight alginate, e.g., 50,000–80,000 daltons, is more easily removed from the intracapsular volume by diffusion through a membrane of sufficient porosity and is therefore preferred. Other useable polymers include acidic fractions of guar gum, carageenan, pectin, tragacanth gum, or xanthan gum.

These materials comprise glycoside-linked saccharide chains. Their free acid groups are often present in the alkali metal ion, e.g., sodium form. If a multivalent ion such as calcium or aluminum is exchanged for the alkali metal ion, the water-soluble polysaccharide molecules are "cross-linked" to form a water-insoluble, shape-retaining gel which can be resolubilized on removal of the multivalent ions by ion exchange or via a sequestering agent. While essentially any multivalent ion which can form a salt with the acidic gum is operable, it is preferred that physiologically compatible ions, e.g., calcium, be employed. This tends to preserve the tissue in the living state. While other multivalent cations can be used, magnesium ions are found to be ineffective in gelling sodium alginate.

A typical protocol for forming the microcapsules comprises first suspending the calls in a 0.5 to 2.5 percent (w/v) solution of the chosen polymer in physiological saline. When using sodium alginate, a 0.6 to 2.4 percent (w/v) solution has been used with success. Next, the polymer solution containing the cells is formed into droplets of a desired size and the droplets are immediately gelled to form shape-retaining masses, preferably but not necessarily, in spherical or spheroidal form. The drop formation may be conducted by known methods such as the following exemplary procedure.

A tube containing an aqueous solution of multivalent cations, e.g., 1.5% $CaCl_2$ (w/v) solution, is fitted with a stopper which holds a drop-forming apparatus. The apparatus consists of a housing having an upper air intake nozzle and an elongate hollow body friction fitted into the stopper. A 10 cc syringe equipped with a stepping pump is mounted atop the housing with a needle, e.g., a 0.01 inch I.D. Teflon coated needle, passing through the length of the housing. The interior of the housing is designed such that the tip of the needle is subjected to a constant laminar air flow which acts as an air knife. In use, with the syringe full of solution containing the material to be encapsulated, the stepping pump is actuated to incrementally force droplets of solution from the tip of the needle. Each drop is "cut off" by the air stream and falls approximately 2.5 cm into the $CaCl_2$ solution where it is immediately gelled by absorption of calcium ions. The distance between the tip of the needle and the surface of the $CaCl_2$ solution is great enough, in this instance, to allow the sodium alginate/cell suspension to assume the most physically favorable shape; a sphere (maximum volume for minimum surface area). Air within the tube bleeds through an opening in the stopper. This procedure results in "cross-linking" of the gel and in the formation of a high viscosity shape-retaining protective temporary matrix containing the suspended tissue and its medium. The matrices collect in the solution as a separate phase and may be separated by aspiration.

In the next step, a semipermeable membrane is deposited about the surface of the temporary matrix by "cross-linking" surface layers. This may be effected by subjecting the gelled temporary matrix to an aqueous solution of a polymer containing cationic groups reactive with anionic functionalities in the gel molecules. Polymers containing acid reactive groups such as free imine or amine groups are preferred. In this situation, the polysaccharide gum is cross-linked by interaction (salt bond formation) between the carboxyl groups and the imine or amine groups. Permeability can be controlled within limits by selecting the molecular weight of the cross-linking polymer used and by regulating the concentration of the polymer solution and the duration of exposure. A solution of polymer having a low molecular weight, in a given time period, will penetrate further into the temporary capsules than will a high molecular weight polymer. The degree of penetration of the cross-linker has been correlated with the resulting permeability. In general, the higher the molecular weight and the less penetration, the larger the pore size. Broadly, polymers within the molecular weight range of 3,000 to 100,000 daltons or greater may be used, depending on the duration of the reaction, the concentration of the polymer solution, and the degree of permeability desired. One successful set of reaction conditions, using polylysine of average molecular weight of about 35,000 daltons, involved reaction for two minutes, with stirring, of a physiological saline solution containing 0.0167 percent polylysine. This results in a capsule membrane having an upper limit of permeability of about 100,000 daltons. Optimal reaction conditions suitable for controlling permeability in a given system can readily be determined empirically in view of the foregoing guidelines. Using this method it is possible to set the upper permeability limit of the membranes at a selected level.

Examples of suitable cross-linking polymers include proteins and polypeptides, either natural or synthetic, having free amino or imino groups, polyethyleneamines, polyethyleneimines, and polyvinyl amines. Polylysine, in both the D and L forms, has been used with success. Proteins such as polyarginine, polycitrulline, or polyornithine are also operable. Polymers in the higher range of positive charge density, e.g., polyvinylamine, vigorously adhere to the anionic groups of the gel molecules to form stable molecules and the capsule membranes are more difficult to disrupt.

An additional coating of cationic polymer or gum can be used to further control pore size. This additional coating can be the same polymer used to form the temporary matrix or any of the polymers described above, e.g., a polyvinylamine coating could be used on sodium alginate/poly-l-lysine microcapsules.

Treatment with a dilute solution of gel will tie up free amino groups on the surfaces of the capsules which otherwise may impart to the capsules a tendency to clump.

At this point in the encapsulation, capsules collected comprise a semipermeable membrane surrounding a gelled solution of polymer, cell-type compatible culture medium and a cell. Since mass transfer should be promoted within the capsule and across the capsule membrane, it is preferred to reliquify the gel to its water-soluble form. This may be done by reestablishing the conditions under which the gel is a liquid, e.g., removing the calcium or other multifunctional cations from the interior gel. The medium in the capsule can be resolubilized simply by immersing the capsule in phosphate buffered saline which contains alkali metal ions and hydrogen ions. Monovalent ions exchange with the calcium or other multifunctional ions within the gel when the capsule is immersed in the solution with stirring. Sodium citrate solutions may be used for the same purpose, and serve to sequester the divalent ions.

Cell cultures encapsulated as described above may be suspended in a culture medium designed specifically to satisfy all of the requirements of the particular cell type involved and will continue to undergo normal metabolism. Typically, the components normally used to promote growth of cells are relatively low molecular weight species and readily diffuse across the capsule membrane into the microenvironment of the cell where they permeate the cell membrane. Products of metabolism of the cell which are secreted into the intracapsular medium, if they have a molecular weight below the upper limit of permeability of the capsule membrane, likewise diffuse thereacross and collect in the extracapsular medium.

The encapsulated cell may be cultured under conditions of temperature, pH, and ionic environment, identical to conventional cultures. The growth rate of the culture is unimpaired by the microencapsulation process. The cell culture fills the capsule with cells but does not rupture the capsule membrane.

LYSING THE CELLS

After the culture has grown, the majority of the non-secreted substance of interest is still contained within the cells. In order to obtain this substance, the cells are removed from the culture growth medium and the cell membrane is lysed without disturbing the capsule membrane. The preferred method of lysis is resuspending the cells in a detergent which does not disrupt the capsule membrane but lyses the cell membrane. A number of detergents including sodium dodecyl sulphate, sodium deoxycholate and nonionic detergents such as Tween 80, Triton X-100 and NP40 have been used with success but the preferred detergent for use with prokaryotic cells is 2M guanidine hydrochloride. Surprisingly, detergents designed to disrupt ionic interactions such as sodium dodecyl sulphate, sodium deoxycholate and guanidine hydrochloride do not disrupt the microcapsule membrane and in fact are preferred for applications involving prokaryotic cells.

In a typical procedure, the capsules are separated from the culture medium by aspiration, washed with buffered saline, and mixed with an equal volume of e.g., 4M guanidine hydrochloride. The suspension is diluted with 2M guanadine hydrochloride until the capsules are about 1/10 of the total fluid volume. The suspension is then incubated at 37° C. and the product is collected from the supernatant.

The following nonlimiting examples will further explain the process of the invention and demonstrate its efficacy.

EXAMPLE 1

This example demonstrates the effectiveness of the process of the invention for prokaryotic cells by comparing the encapsulation technique with the standard culturing technique, i.e., monodisperse suspensions for a genetically modified bacteria. The bacteria used in the experiment, $HB_{101}/pBR_{322}$-$amp^r$, is an *E. coli* (strain K-12) modified by the introduction of the penicillinase producing plasmid, $pBR_{322}$. This bacteria, which is ampicillin resistent, is illustrative of the genetically modified cells useful with the present invention. $HB_{101}$ produces a pyrogenic lipopolysaccharide, an endotoxin with an average molecular weight in excess of about $5 \times 10^4$ daltons. This endotoxin is the major problem in purification of products intended for in vivo use. Only about 20 percent of the penicillinase is secreted by the cells, the rest is retained within the cell. Penicillinase produced from the plasmid $pBR_{322}$ has a molecular weight of about $3 \times 10^4$ daltons.

The first step of the process is encapsulating the cell. A culture of $HB_{101}/pBR_{322}$-$amp^r$ was incubated overnight from frozen stock in standard Luria broth (LB). The LB broth contained 10 gm/l trytone (Difco Laboratories), 5 gm/l yeast extract (Difco), 10 gm/l sodium chloride (Sigma Chemical Company) and 25 mg/l ampicillin (Sigma). The medium was made by dissolving the above ingredients and filter sterilizing the mixture through a 0.22 micrometer filter (Gelman Laboratories). This medium promotes growth of the $HB_{101}$ cells while eliminating other non-ampicillin resistant strains.

One milliliter of the suspension was centrifuged for three minutes in a Brinkmann 3200 microfuge resulting in a small bacterial pellet. The bacteria were resuspended in 0.2 ml of 0.15M sodium chloride and mixed thoroughly into 20 ml of 1.6 percent (w/v) sodium alginate (Kelco LV, lot #55072A) solution. The temporary matrices were produced by forcing the alginate-bacteria mixture through a droplet forming apparatus (as previously described) and contacting the resulting liquid microspheres with a 1.2 percent (w/v) $CaCl_2$ solution gelling the alginate. The temporary matrices were washed repeatedly with a 0.15M sodium chloride solution and placed in a 0.5 g/l poly-l-lysine (Sigma, $6.5 \times 10^4$ dalton molecular weight) solution for six minutes to form the capsule membrane. The capsules were then washed in a 0.2 percent (w/v) $CaCl_2$, 0.014 percent (w/v) CHES buffer, pH 7.4 (N-cyclohexylamino ethane sulfonic acid, Sigma) followed by a 0.2% $CaCl_2$ (w/v) wash. A second coating of polyvinylamine (PVA) was added by placing the capsules in a 0.6% (w/v) PVA (Polysciences) in saline for five minutes. The capsules were then washed twice in saline and placed in a 0.06% (w/v) sodium alginate/saline solution for four minutes. After two additional saline washes, the capsules were washed twice in 55 mM sodium citrate-saline solution, the first wash for sixteen minutes and the second for six minutes. After two additional saline washes, the capsules were resuspended in fresh LB broth which had sodium citrate added to a final concentration of 10 mM, in order to prevent regelling of the alginate. The cells were incubated for 24 hours at 37° C. before harvesting.

Figure 1:
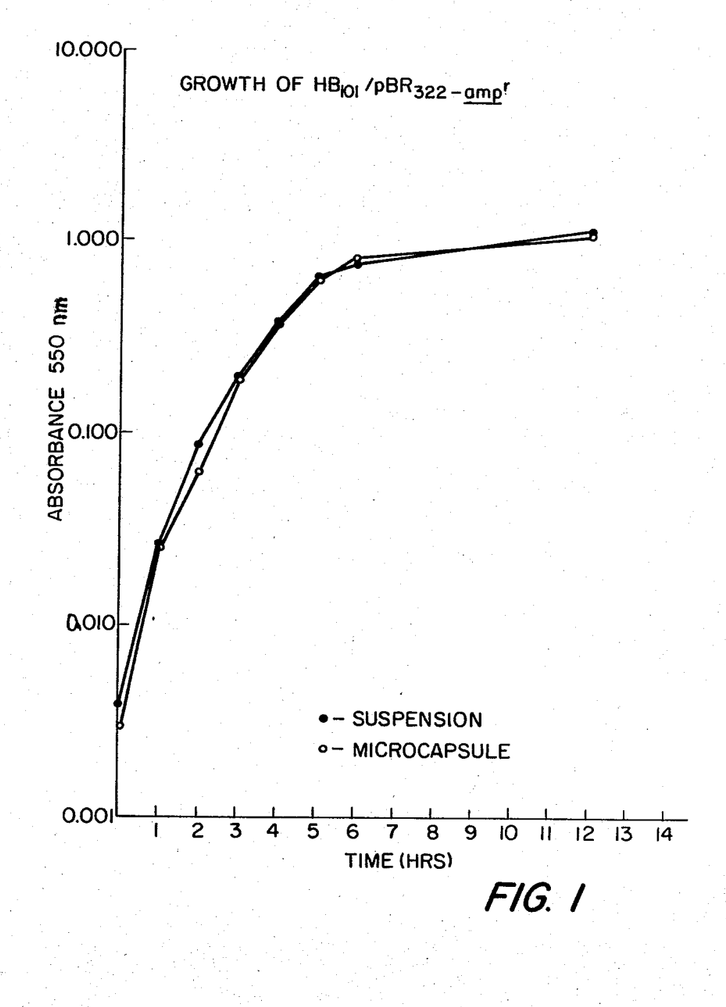
FIG. 1 depicts a growth curve of genetically modified pyrogen containing bacteria which produces the enzyme penicillinase. The graph illustrates that the encapsulation of the bacteria does not adversely affect the growth rate as compared with a conventional suspension culture.

FIG. 1 illustrates the comparative growth rates for the encapsulated cells versus and a conventional suspension culture. Samples of both cultures were taken at various intervals and the growth rate was determined by measuring the 550 nm absorption. The growth rates were virtually identical illustrating that the encapsulation technique does not adversely affect the viability of the cells. The capsules had an average size of about 800 microns and each capsule contains up to about $10^5$ cells.

After growth of the cell culture, the capsules were separated from the LB broth by aspiration and washed repeatedly with sterile phosphate buffered saline (PBS). The volume of the capsules was measured and an equal amount of 4M guanidine hydrochloride (Sigma) in PBS was added. The resultant suspension was diluted with 2M guanidine hydrochloride until the capsule volume was about ten percent of the fluid volume. The capsules were incubated at 37° C. in a Costar T-150 culture flask and samples were taken at various intervals of the supernatant and of the capsules. At each interval, 3 ml of the suspended capsule solution was withdrawn from the culture using a pipet. The supernatant was drawn off as one sample and an equal volume of fresh 2M guanidine hydrochloride was added to the capsules. The capsule membrane was disrupted using a Wheaton 7 ml dounce homogenizer. A table top centrifuge was used to spin down the capsule membrane and cell membrane fragments and the resultant supernatant was taken as the intracapsular sample.

Each sample was tested for both enzyme concentration and endotoxin concentration. To test for enzyme concentration, the sample was diluted with water to a volume of 1 ml and 1 ml of 1% gelatin in water was added. The gelatin/sample mixture was then added to 5 ml of 2 mg/l Penicillin G in phosphate buffer, pH 6.5, and incubated for 30 minutes at 30° C. Ten milliliters of a mixture of 0.017N iodine, 0.6M potassium iodide, and 1.75M sodium acetate, pH 4.0, was added to the mixture and allowed to incubate an additional 10 minutes. The resulting colored solution was titrated with a 0.017N sodium thiosulfate until the color disappeared completely. The assay is based on the reaction between penicilloic acid and free iodine. The penicillinase present in the sample reacts with the added penicillin to form penicilloic acid. The penicilloic acid then reacts with free iodine, stripping the iodine from the solution. Sodium thiosulfate also reacts with free iodine so the amount of thiosulfate needed to remove the color is a measure of the amount of penicilloic acid in solution and indirectly a measure of the penicillinase activity. The less thiosulfate needed to clarify the solution, the more penicillinase activity was present in the original solution. The penicillinase activity is measured by the units of penicillin converted to penicilloic acid per unit time.

The endotoxin concentration is assayed by placing 100 ml of endotoxin solution, diluted with sterile water, in a sterile test tube and adding an equal volume of Limulus-Amoebocytek-Lysate (LAL, Cape Cod Associates) in water. The tube is incubated for one hour at 37° C. and observed for clot formation. If a clot is formed which will not dislodge by inversion of the tube, there is a positive indication of endotoxin. The sample is serially diluted to give a numerical value.

Figure 2:
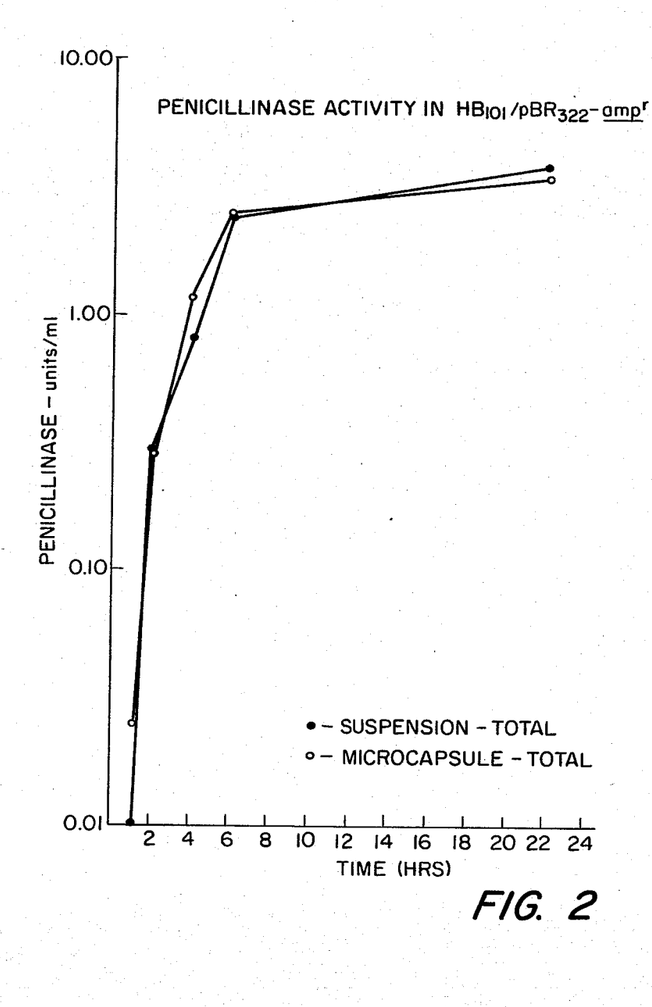
FIG. 2 is a graph illustrating that the intracellular production of the substance of interest is substantially identical irrespective of whether the cells are grown in a conventional suspension culture or in an encapsulated culture.

FIG. 2 is a graph of total penicillinase activity, comparing the encapsulated culture with a conventional suspension culture. The total penicillinase activity for the cultures is virtually identical, illustrating that the encapsulation technique does not adversely affect penicillinase production.

Figure 3:
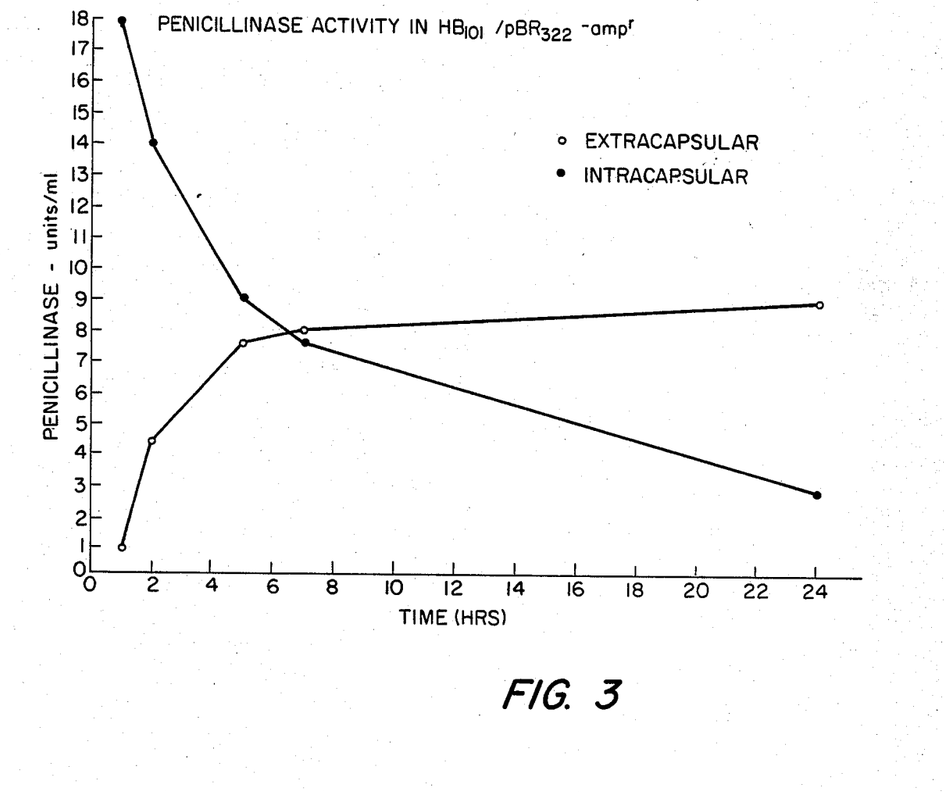
FIG. 3 is a graph illustrating the kinetics of release of penicillinase through the semipermeable capsule membrane after lysing of the cell membrane.

FIG. 3 illustrates the diffusion rate of the penicillinase through the semipermeable capsule membrane. The capsules were placed in 2M quanidine hydrochloride at time zero and the intracapsular and extracapsular fluids were tested for penicillinase activity at various intervals. As is shown in FIG. 3, the initial penicillinase concentration in the supernatent is low but the penicillinase diffuses through the pores in the semipermeable membrane and appears in the extracapsular medium over time. The intracapsular concentration of penicillinase is reduced, showing actual transfer of penicillinase through the capsule membrane.

Figure 4:
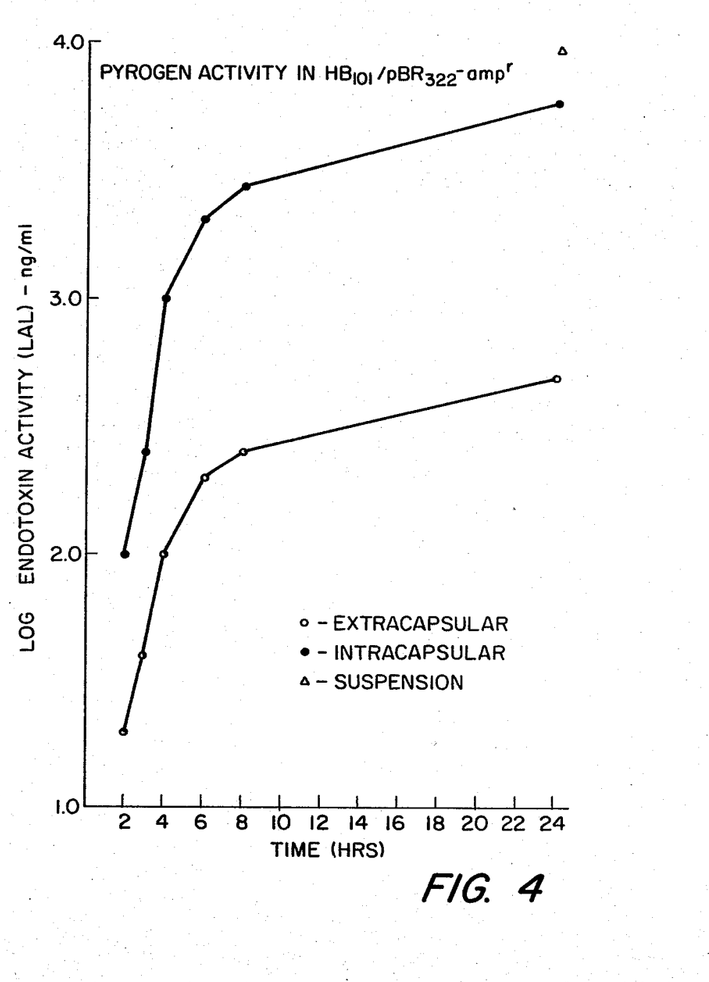
FIG. 4 is a graph illustrating pyrogen concentration in the extracapsular fluid, the intercapsular fluid and in a conventional suspension culture media after lysing the cells.

FIG. 4, particularly when taken in conjunction with FIG. 3, illustrates the effectiveness of the invention; the formation of a barrier against pyrogen transport while allowing enzyme transport across the capsule membrane. FIG. 4 shows that the extracapsular concentration of endotoxin is at least one order of magnitude lower than the intracapsular concentration. These figures indicate that the capsule membrane hinders the passage of the endotoxin while allowing free transport of the penicillinase, facilitating recovery of the penicillinase from the culture. FIG. 4 also shows that the supernatant from conventional cultures has about 100-fold more endotoxin than is present in the extracapsular fluid of the present invention.

EXAMPLE 2

This example demonstrates that the process disclosed herein is effective for eukaryotic as well as prokaryotic cells. The cell line used in this experiment was the Friend Erythroleukemic cell line (FEL$_{745}$) a mouse erythroleukemia line which grows readily in a suspension culture. FEL$_{745}$ cells are induced to produce hemoglobin upon treatment with dimethylsulfoxide (DMSO). The produced hemoglobin has a molecular weight of about $6.3 \times 10^4$ daltons and is substantially retained within the cell until cell lysis.

The experiment compares cell viability and ease of hemoglobin purification in encapsulated versus suspension cultures. A culture of FEL$_{745}$ cells was centrifuged for five minutes in a microfuge and the resulting pellet was resuspended in a 1.2 percent (w/v) sodium chloride (Sigma). A temporary matrix was produced by forcing the alginate-cell mixture through a droplet forming apparatus (as previously described) and contacting the resulting liquid microspheres with a 1.02% (w/v) CaCl$_2$ solution gelling the alginate. The resulting temporary matrix was washed twice, first in 5 mM CHES buffer, pH 7.5, in 75 mM CaCl$_2$, and then in a second 75 mM CaCl$_2$ wash. Addition of a 0.05% (w/v) solution of poly-1-lysine (Miles Laboratories, molecular weight 42,600 daltons), 0.15M NaCl for 3 minutes with agitation forms the permanent capsule membrane. The resulting capsules were washed 3 times, first with 5 mM CHES buffer, pH 7.5, in 75 mM CaCl$_2$, then with 75 mM CaCl$_2$, and finally with 0.15M NaCl. The capsules were incubated for 4 minutes with 0.03% (w/v) sodium alginate in saline and then washed twice with the culture medium, RPMI-1640 (Flow Labs) containing 10% (w/v) fetal calf serum (FCS) (Flow Labs) and antibiotics. The microcapsules were placed into tissue culture flasks with the culture medium and incubated at 37° C. in a 5% CO$_2$ atmosphere.

Figure 5:
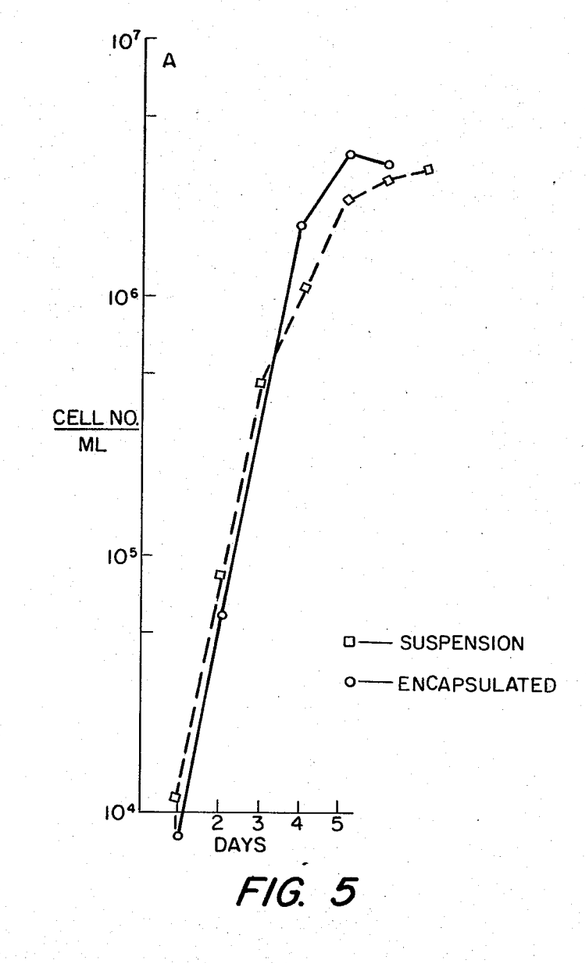
FIG. 5 depicts a growth curve of a eukaryotic cell culture. The graph illustrates that the encapsulation technique does not adversely affect the growth rate as compared with a conventional suspension culture.

FIG. 5 illustrates the comparative growth rates of the encapsulated cells versus a conventional suspension culture. The cultures were sampled at various intervals and a cell count taken. The cell densities for the cultures were virtually identical, indicating the encapsulation technique does not adversely affect cell growth.

Hemoglobin production was induced in the cultures by treatment with DMSO (Mallinkrodt Chemical). Cultures of $8 \times 10^5$ cells/ml density were incubated for 48 hours with 1% DMSO in the culture medium, an additional 24 hours with 1.5% DMSO and a final 24 hours with 2% DMSO. The cultures were washed with 0.15M NaCl and resuspended in five volumes of a lysis buffer containing 50 mM Tris, pH 7.0, 25 mM KCL, 5 mM MgCl$_2$, 1 mM B-mercaptoethanol, and 0.3% (w/v) Triton-100. The cultures were incubated for two 10 minute periods at 4° C. with gentle vortexing before and after each period. The cultures were centrifuged at 10,000$\times$g for 10 minutes at 4° C. and the supernatant fluid collected. Hemoglobin content was assayed spectrophotometrically at 414 nm and total protein was assayed using a standard Lowry procedure.

TABLE 1

|  | A<br>Hemoglobin concentration ug/10$^6$ cells | B<br>Total Protein concentration ug/10$^6$ cells | A/B |
|---|---|---|---|
| Suspension control | 2.59 | 25.2 | 0.102 |
| Intact microcapsules | 3.18 | 9.6 | 0.331 |

Table 1 illustrates the effectiveness of the process of the invention. The amount of homoglobin produced by the suspension and the encapsulated cultures is approximately equal but the hemoglobin/protein (A/B) ratio for the encapsulated culture is more than three times the A/B ratio for the suspension culture. The A/B ratio is a measure of the specific homoglobin activity of the supernatant. This experiment shows that the microcapsules retain the high molecular weight proteins, lipids, polysaccharides and nucleic acids thereby yielding higher specific activity of the substance of interest.

While the method described herein as most useful if the nonsecreted substance of interest has a relatively small molecular weight, it will also work for any system which includes a substantially nonsecreted substance and a larger molecular weight contaminant. Those skilled in the art may find other variations to the process or other embodiments which accomplish the invention taught herein. Such other variations and embodiments are within the following claims.

What is claimed is:

1. A process for recovering a non-secreted substance produced by living cells and for recovering said substance as a crude product having a reduced concentration of high molecular weight contaminants, said process comprising the steps of:
   A. encapsulating cells within a capsule membrane have permeability properties which permit passage of a non-secreted substance but retard passage of high molecular weight contaminants;
   B. suspending said encapsulated cells in an aqueous culture medium;
   C. allowing said cells to undergo metabolism within said capsule membrane;
   D. lysing the cell membranes of said cells without disrupting said capsule membrane;
   E. allowing said substance to diffuse preferentially through said capsule membrane into an extracaspular fluid, and
   F. harvesting said substance from said extracapsular fluid.

2. The process of claim 1 wherein said encapsulation step (A) is effected by forming said capsule membrane by reaction between plural cationic groups on polymer chains and plural anionic groups on a water-soluble polymer to form a water-insoluble salt bonded matrix.

3. The process of claim 1 wherein said encapsulation step (A) is effected by the steps of:
   (a) suspending the cells in an aqueous medium physiologically compatible therewith and containing a water-soluble polymer having plural anionic moieties;
   (b) forming the suspension into a droplet containing the cell;
   (c) subjecting the droplet to a solution of multivalent, physiologically compatible cations to gel the droplet as a discrete, shape-retaining, water-insoluble temporary matrix; and
   (d) cross-linking surface layers of said temporary matrix to produce a semipermeable capsule membrane about said droplet by subjecting it to a polymer comprising plural cationic groups reactive with said anionic moieties.

4. The process of claim 3 comprising the additional step of resolubilizing the gel within said capsule membrane after step (d).

5. The process of claim 1 wherein said aqueous culture medium is a cell growth medium sufficient to support biosynthesis of said substance.

6. The process of claim 5 wherein said cell growth medium is sufficient to support mitosis of said encapsulated cells.

7. The process of claim 6 comprising the additional step of allowing said cells to undergo mitosis within said capsule membrane between steps C and D to produce a cell colony substantially filling the volume within said capsule membrane without rupturing said capsule membrane.

8. The process of claim 1 wherein the lysing of said cell membranes is effected by suspending said encapsulated cells in a detergent.

9. The process of claim 8 wherein said detergent is an aqueous solution of a detergent selected from a group consisting of nonionic surfactants, guanidine hydrochloride, sodium dodecyl sulfate, sodium deoxycholate, and mixtures thereof.

10. The process of claim 1 wherein said cells are prokaryotic cells.

11. The process of claim 10 wherein said contaminant comprises a pyrogen.

12. The process of claim 11 wherein said capsule membrane is substantially impermeable to said pyrogen.

13. The process of claim 11 wherein said pyrogen comprises an endotoxin.

14. The process of claim 11 wherein said pyrogen has a molecular weight greater than about $5 \times 10^4$ daltons.

15. The process of claim 1 wherein said cells comprise genetically modified cells.

16. The process of claim 15 wherein said contaminant comprises a pyrogen.

17. The process of claim 16 wherein said capsule membrane is substantially impermeable to said pyrogen.

18. The process of claim 16 wherein said pyrogen comprises an endotoxin.

19. The process of claim 16 wherein said pyrogen has a molecular weight greater than about $5 \times 10^4$ daltons.

20. The process of claim 1 wherein during said encapsulation step (A), spheroidal microcapsules having a diameter from about 0.1 to 1.0 millimeters are produced.

21. The process of claim 1 wherein said capsule membrane has an upper limit of permeability greater than the molecular weight of said substance and lower than the molecular weight of said high molecular weight contaminant.

22. The process of claim 1 wherein said capsule membrane defines a multiplicity of tortuous-path pores, and the rate at which said pores allow passage of a molecule is an inverse function of the molecular weight of said molecule.

23. A process for recovering a nonsecreted substance produced by genetically modified prokaryotic cells, and for recovering the substance as a crude product having a reduced concentration of high molecular weight pyrogens, said process comprising the steps of:
   A. encapsulating genetically modified prokaryotic cells within an enclosed capsule defining an intracapsular volume, said capsule comprising a capsule membrane defining a multiplicity of tortuous-path pores which permit passage of a non-secreted substance while retarding the passage of a pyrogen;
   B. suspending said encapsulated cells in an aqueous culture medium;
   C. allowing said cells to undergo metabolism within said capsule membrane;
   D. lysing the cell membranes of said cells without disrupting said capsule membrane;
   E. allowing said substance to diffuse through the pores of said capsule membrane into an extracapsular fluid; and
   F. harvesting said substance from said extracapsular fluid.

24. The process of claim 23 comprising the additional step of culturing said cells within said capsule membrane to produce a cell colony which substantially fills said intracapsular volume without rupturing said capsule membrane.

25. The process of claim 23 wherein the lysing of said cell membranes is effected by suspending said encapsulated cells in a detergent.

26. The process of claim 25 wherein said detergent is an aqueous solution of a detergent selected from a group consisting of non-ionic surfactants, guanidine hydrochloride, sodium dodecyl sulfate, sodium deoxycholate, and mixtures thereof.

27. The process of claim 23 wherein said encapsulation step (A) is effected by forming said capsule membrane by reaction between plural cationic groups on polymer chains and plural anionic groups on a water-soluble polymer to form a water-insoluble salt bounded matrix.

28. The process of claim 23 wherein said encapsulation step (A) is effected by the steps of:

(a) suspending the cells in aqueous medium physiologically compatible therewith and containing a water-soluble polymer having plural anionic moieties;
(b) forming the suspension into a droplet containing the cells;
(c) subjecting the droplet to a solution of multivalent, physiologically compatible cations to gel the droplet as a discrete, shape-retaining, water-insoluble temporary matrix; and
(d) cross-linking surface layers of said temporary matrix to produce a semipermeable capsule membrane about said droplet by subjecting it to a polymer comprising plural cationic groups reactive with said anionic moieties.

29. The process of claim 28 comprising the additional step of resolubilizing the gel within said capsule membrane after step (d).

* * * * *